(12) United States Patent
Coburn et al.

(10) Patent No.: US 7,371,853 B2
(45) Date of Patent: May 13, 2008

(54) MACROCYCLIC β-SECRETASE INHIBITORS FOR THE TREATMENT OF ALZHEIMER'S DISEASE

(75) Inventors: Craig A. Coburn, Royersford, PA (US); Shawn J. Stachel, Perkasie, PA (US); Joseph P. Vacca, Telford, PA (US)

(73) Assignee: Merck & Co., Inc., Rahway, NJ (US)

( * ) Notice: Subject to any disclaimer, the term of this patent is extended or adjusted under 35 U.S.C. 154(b) by 182 days.

(21) Appl. No.: 10/541,476

(22) PCT Filed: Jan. 2, 2004

(86) PCT No.: PCT/US2004/000085

§ 371 (c)(1),
(2), (4) Date: Jul. 6, 2005

(87) PCT Pub. No.: WO2004/062625

PCT Pub. Date: Jul. 29, 2004

(65) Prior Publication Data

US 2006/0058278 A1    Mar. 16, 2006

Related U.S. Application Data

(60) Provisional application No. 60/438,630, filed on Jan. 7, 2003.

(51) Int. Cl.
| C07D 267/22 | (2006.01) |
| C07D 281/18 | (2006.01) |
| C07D 291/00 | (2006.01) |
| C07D 337/16 | (2006.01) |
| C07D 487/00 | (2006.01) |
| C07D 498/00 | (2006.01) |
| C07D 513/00 | (2006.01) |

(52) U.S. Cl. ..................................... 540/456
(58) Field of Classification Search ............ None
See application file for complete search history.

(56) References Cited

U.S. PATENT DOCUMENTS 6,525,074 B2    2/2003   deSolms et al.
7,067,507 B2 *  6/2006   Pulley et al. ............. 514/183

FOREIGN PATENT DOCUMENTS

| EP | 1 186 305 | 3/2002 |
| WO | WO 89/04833 | 6/1989 |
| WO | WO 01/00665 | 1/2001 |
| WO | WO 02/100399 | 12/2002 |
| WO | WO 02/100856 | 12/2002 |
| WO | WO 03/257721 | 7/2003 |
| WO | WO 03/072535 | 9/2003 |

OTHER PUBLICATIONS

Coburn et al., "Identification of a Small Molecule Nonpeptide Active Site Beta-Secretase Inhibitor That Displays a Nontraditional Binding Mode forAspartyl Proteases," J. Med. Chem., vol. 47, pp. 6117-6119 (2004).

* cited by examiner

Primary Examiner—James O. Wilson
Assistant Examiner—Noble Jarrell
(74) Attorney, Agent, or Firm—William Krovatin; John C. Todaro

(57) ABSTRACT

The present invention is directed to compounds of formula (I)

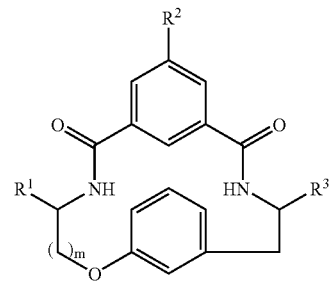

which are inhibitors of the beta-secretase enzyme and that are useful in the treatment or prevention of diseases in which the beta-secretase enzyme in involved, such as Alzheimer's disease. The invention is also directed to pharmaceutical compositions comprising these compounds and the use of these compounds and compositions in the prevention or treatment of such diseases in which the beta-secretase enzyme is involved.

13 Claims, No Drawings

MACROCYCLIC β-SECRETASE INHIBITORS FOR THE TREATMENT OF ALZHEIMER'S DISEASE

CROSS REFERENCE TO RELATED APPLICATIONS

This application is a U.S. National Phase application under 35 U.S.C. § 371 of PCT Application No. PCT/US2004/000085, filed Jan. 2, 2004, which claims priority under 35 U.S.C. § 119(e) from U.S. Provisional Application Ser. No. 60/438,630, filed Jan. 7, 2003.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production Aβ, and accumulation of β amyloid plaques in the brain, which is characteristic of Alzheimer's disease (see R. N. Rosenberg, Arch. Neurol., vol. 59, September 2002, pp. 1367-1368; H. Fukumoto et al, Arch. Neurol., vol. 59, September 2002, pp. 1381-1389; J. T. Huse et al, J. Biol. Chem., vol 277, No. 18, issue of May 3, 2002, pp. 16278-16284; K. C. Chen and W. J. Howe, Biochem. Biophys. Res. Comm, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds that are inhibitors of the β-secretase enzyme that are useful in the treatment or prevention of diseases in which the β-secretase enzyme is involved, such as Alzheimer's disease. The invention is also directed to pharmaceutical compositions comprising these compounds and the use of these compounds and compositions in the prevention or treatment of such diseases in which the β-secretase enzyme is involved.

DETAILED DESCRIPTION OF THE INVENTION

The present invention is directed to compounds of the formula I:

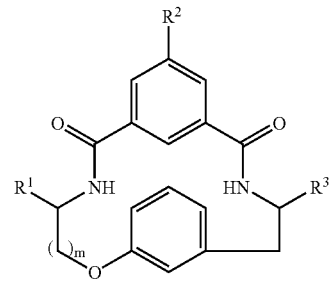

wherein:
$R^1$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
 (a) halo,
 (b) hydroxy,
 (c) —O—$C_{1-6}$alkyl,
 (d) —$C_{3-6}$cycloalkyl,
 (e) phenyl or biphenyl, which is unsubstituted or substituted with 1-5 substituents where the substituents are independently selected from:
  (i) —$C_{1-6}$alkyl,
  (ii) —$C_{3-6}$cycloalkyl,
  (iii) —O—$C_{1-6}$alkyl,
  (iv) halo,
  (v) hydroxy,
  (vi) —$CF_3$,
  (vii) —$OCF_3$,
  (viii) —$NR^9R^{10}$, and
  (ix) —CN,
 (f) —$CO_2R^9$, wherein $R^9$ is independently selected from:
  (i) hydrogen,
  (ii) —$C_{1-6}$alkyl, which is unsubstituted or substituted with 1-6 fluoro,
  (iii) benzyl, and
  (iv) phenyl,
 (g) —$NR^9R^{10}$, wherein $R^{10}$ is independently selected from:
  (i) hydrogen,
  (ii) —$C_{1-6}$alkyl, which is unsubstituted or substituted with 1-6 fluoro,
  (iii) benzyl, and
  (iv) phenyl,
 (h) -$CONR^9R^{10}$,
(3) phenyl which is unsubstituted or substituted with 1-5 substituents where the substituents are independently selected from:
 (a) —$C_{1-6}$alkyl,
 (b) —$C_{1-6}$alkyl-phenyl, (c) —$C_{3-6}$cycloalkyl,
(d) —O—$C_{1-6}$alkyl,
(e) halo,
(f) hydroxy,
(g) —$CF_3$,
(h) —$OCF_3$,
(i) —$NR^9R^{10}$, and
—CN;

$R^2$ is selected from the group consisting of:
(1) hydrogen,
(2) $R^4$—$S(O)_p$-,
  wherein $R^4$ is independently selected from the group consisting of:
  (a) —$C_{1-6}$alkyl, which is unsubstituted or substituted with 1-6 fluoro,
  (b) phenyl, and
  (c) benzyl,
  and wherein p is independently 0, 1, or 2,
(3) $R^4$—$S(O)_pN(R^5)$-,
  wherein $R^5$ is independently selected from the group consisting of:
  (a) hydrogen,
  (b) —$C_{1-6}$alkyl, which is unsubstituted or substituted with 1-6 fluoro,
  (c) phenyl, and
  (d) benzyl,
(4) —CN,
(5) —$C_{1-6}$alkyl-CN,
(6) halogen, (7)

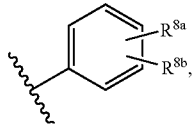

wherein $R^{8a}$ and $R^{8b}$ are independently selected from the group consisting of:
(a) hydrogen,
(b) —CN,
(c) halo,
(d) —$C_{1-6}$alkyl,
(e) —O—$R^5$,
(f) —S—$R^5$,
(g) —$CO_2R^5$, and
(h) tetrazolyl, (8)

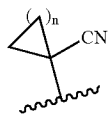

wherein n is 1, 2, 3 or 4;

$R^3$ is selected from the group consisting of:
(1) —CH(OH)—$R^6$,
(2) —C(O)$R^6$,
(3) —CH($R^6$)—$NR^7R^9$, and
(4) —C(O)—$NR^7R^9$;

$R^6$ is independently selected from the group consisting of:
(1) hydrogen
(2) $C_{1-6}$ alkyl, (3)

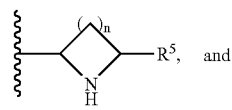

and (4)

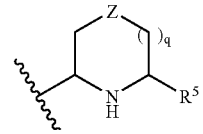

wherein Z is selected from the group consisting of —C(O)—, —CH(OH)—, and

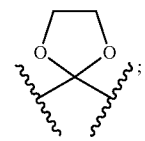

and wherein q is 1 or 2;

$R^7$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or biphenyl, which is unsubstituted or substituted with 1-5 substituents where the substituents are independently selected from:
    (i) —$C_{1-6}$alkyl,
    (ii) —$C_{3-6}$cycloalkyl,
    (iii) —O—$C_{1-6}$alkyl,
    (iv) halo,
    (v) hydroxy,
    (vi) —$CF_3$,
    (vii) —$OCF_3$,
    (viii) —$NR^9R^{10}$, and
    (ix) —CN,
  (f) —$CO_2R_9$,
  (g) —$NR^9R^{10}$,
  (h) —$CONR^9R^{10}$,
(3) —$CHR^5$—$CONR^9R^{10}$,
(4) phenyl which is unsubstituted or substituted with 1-5 substituents where the substituents are independently selected from:
  (a) —$C_{1-6}$alkyl,
  (b) —$C_{1-6}$alkyl-phenyl,
  (c) —$C_{3-6}$cycloalkyl,
  (d) —O—$C_{1-6}$alkyl,
  (e) halo,
  (f) hydroxy,
  (g) —$CF_3$,
  (h) —$OCF_3$,
  (i) —$NR^9R^{10}$, wherein $R^9$ is independently selected from:

(i) hydrogen,
(ii) —$C_{1-6}$alkyl, which is unsubstituted or substituted with 1-6 fluoro,
(iii) benzyl, and
(iv) phenyl,
and wherein $R^{10}$ is independently selected from:
(i) hydrogen,
(ii) —$C_{1-6}$alkyl, which is unsubstituted or substituted with 1-6 fluoro,
(iii) benzyl, and
(iv) phenyl,
(j) —CN;
m is independently 1, 2, 3 or 4;
and pharmaceutically acceptable salts thereof.

In an embodiment of the present invention $R^1$ is selected from the group consisting of:
(1) hydrogen,
(2) —$C_{1-6}$alkyl, which is unsubstituted or substituted with 1-7 substituents where the substituents are independently selected from:
  (a) halo,
  (b) hydroxy,
  (c) —O—$C_{1-6}$alkyl,
  (d) —$C_{3-6}$cycloalkyl,
  (e) phenyl or biphenyl, which is unsubstituted or substituted with 1-5 substituents where the substituents are independently selected from:
    (i) —$C_{1-6}$alkyl,
    (ii) —$C_{3-6}$cycloalkyl,
    (iii) —O—$C_{1-6}$alkyl,
    (iv) halo,
    (v) hydroxy,
    (vi) —$CF_3$,
    (vii) —$OCF_3$,
    (viii) —$NR^9R^{10}$, and
    (ix) —CN,
  (f) —$CO_2R^9$, wherein $R^9$ is independently selected from:
    (i) hydrogen,
    (ii) —$C_{1-6}$alkyl, which is unsubstituted or substituted with 1-6 fluoro,
    (iii) benzyl, and
    (iv) phenyl,
  (g) —$NR^9R^{10}$, wherein $R^{10}$ is independently selected from:
    (i) hydrogen,
    (ii) —$C_{1-6}$alkyl, which is unsubstituted or substituted with 1-6 fluoro,
    (iii) benzyl, and
    (iv) phenyl,
  (h) —$CONR^9R^{10}$,
(3) phenyl which is unsubstituted or substituted with 1-5 substituents where the substituents are independently selected from:
  (a) —$C_{1-6}$alkyl,
  (b) —$C_{1-6}$alkyl-phenyl,
  (c) —$C_{3-6}$cycloalkyl,
  (d) —O—$C_{1-6}$alkyl,
  (e) halo,
  (f) hydroxy,
  (g) —$CF_3$,
  (h) —$OCF_3$,
  (i) —$NR^9R^{10}$, and
  (j) —CN.

In another embodiment of the present invention $R^1$ is selected from the group consisting of:
(1) hydrogen,
(2) methyl,
(3) isopropyl,
(4) isobutyl, and
(5) phenyl.

In an embodiment of the present invention $R^2$ is: $R^4$—$S(O)_2N(R^5)$—,
wherein $R^4$ is independently selected from the group consisting of:
  (a) —$C_{1-6}$alkyl, which is unsubstituted or substituted with 1-6 fluoro,
  (b) phenyl, and
  (c) benzyl,
and wherein $R^5$ is independently selected from the group consisting of:
  (a) hydrogen,
  (b) —$C_{1-6}$alkyl, which is unsubstituted or substituted with 1-6 fluoro,
  (c) phenyl, and
  (d) benzyl.

In another embodiment of the present invention $R^2$ is $CH_3$—$S(O)_2N(CH_3)$—.

In an embodiment of the present invention $R^3$ is selected from the group consisting of:
(1) —CH(OH)—$R^6$,
(2) —C(O)$R^6$, and
(3) —CH($R^6$)—$NR^7R^9$.

In an embodiment of the present invention $R^6$ is:

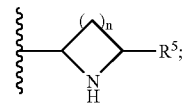

and wherein n is 2 or 3, and $R^5$ is hydrogen or methyl.

In an embodiment of the present invention $R^6$ is:

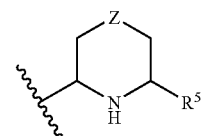

wherein $R^5$ is hydrogen or methyl, and Z is selected from the group consisting of —C(O)—, —CH(OH)—, and

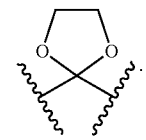

In another embodiment of the present invention $R^3$ is selected from the group consisting of:
(1) —$CH_2$—OH, and
(2) —$CH_2$—NH—CH($CH_2CH_3$)—CO—NH—$CH_2$CH($CH_3$)$_2$.

In an embodiment of the present invention m is 1.
In an embodiment of the present invention m is 2.
Another embodiment of the present invention includes a compound which is selected from the group consisting of:

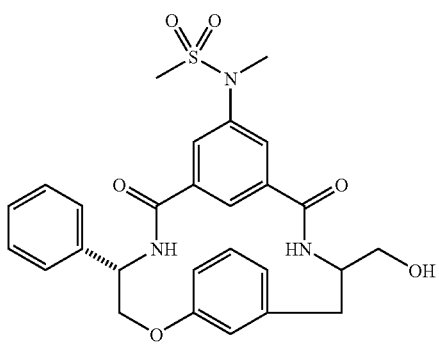
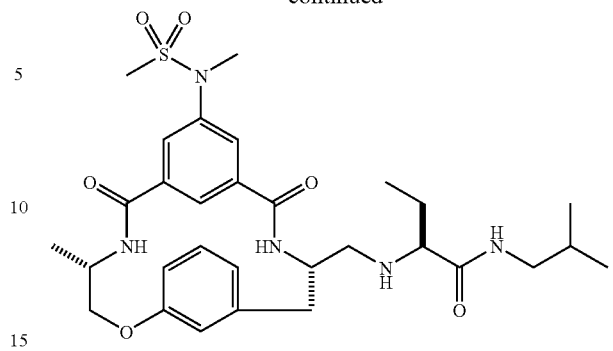
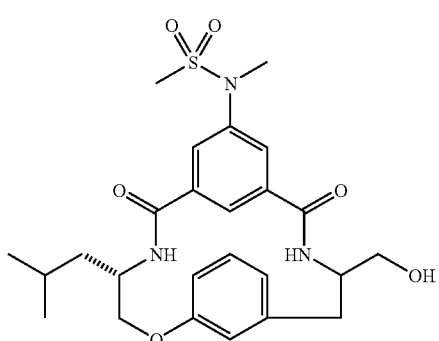
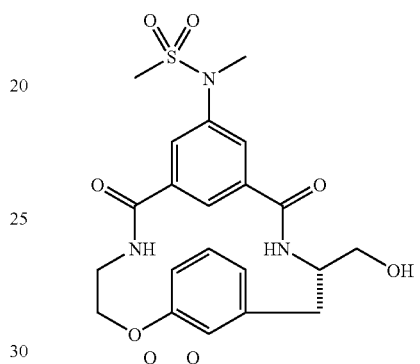
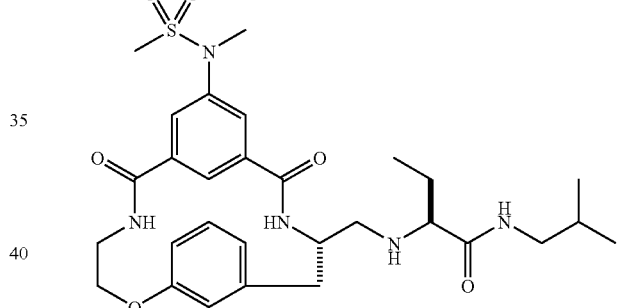
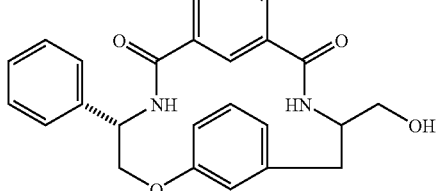
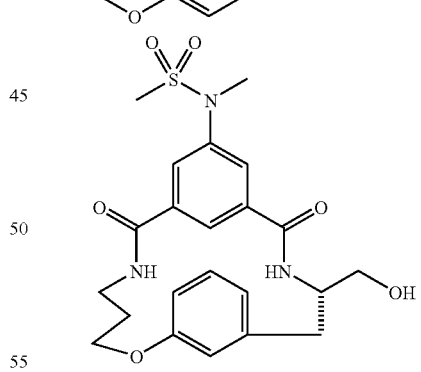
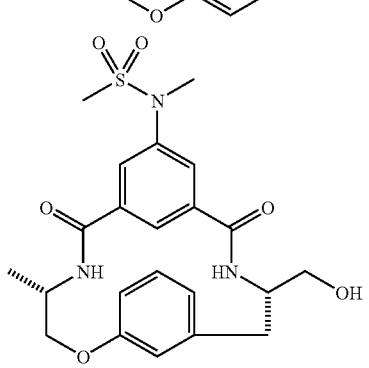

and pharmaceutically acceptable salts thereof.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Schemes 1 and 2.

SCHEME 1

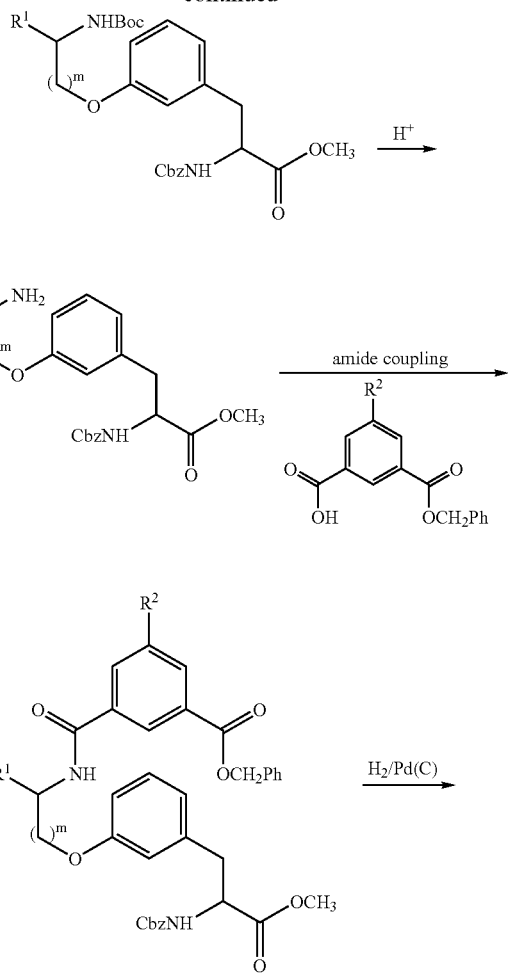

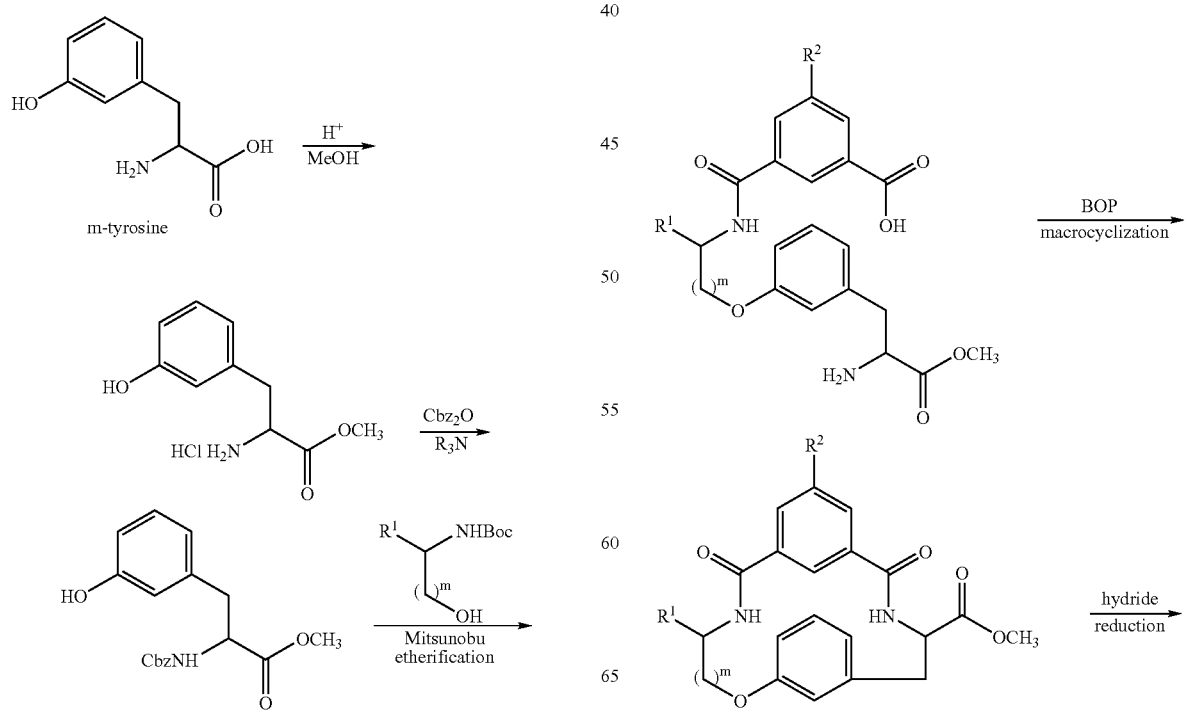

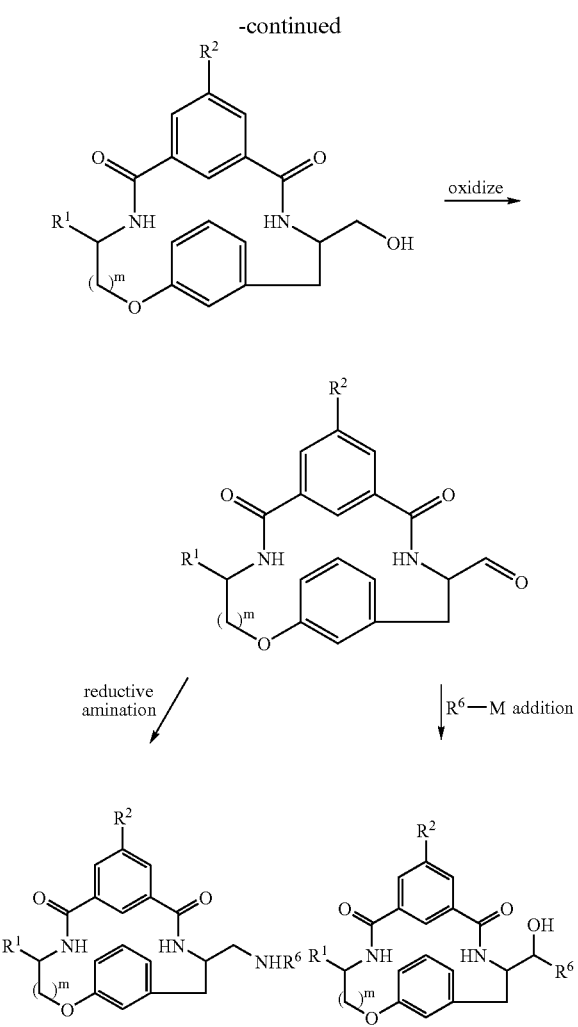

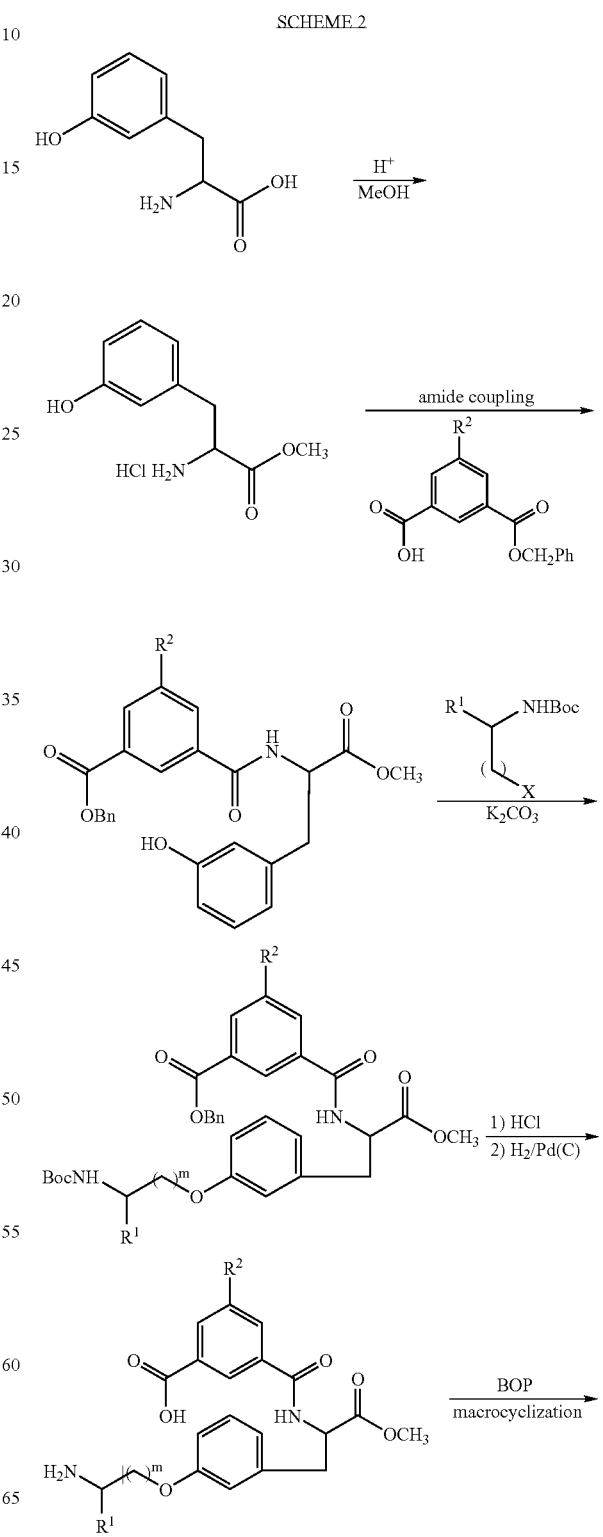

SO₃pyridine in DMSO. The macrocyclic aldehyde can be reductively aminated with an amine and a reducing agent such as NaBH₃CN in a methanolic solvent. The aldehyde may also be reacted with an organometallic agent such as an alkyllithium or Grignard reagent to give the corresponding secondary alcohol.

Referring to Scheme 1, m-tyrosine is converted as described to provide the desired final products. Meta-tyrosine is reacted with thionyl chloride in an alcoholic solvent such as methanol at 0°-70° C. to give the corresponding ester. The amino ester salt is protected with a benzyloxycarbonyl group by the reaction of the amine with Cbz chloride or Cbz anhydride in a solvent such as dichloromethane in the presence of a tertiary amine base such as triethylamine. The phenolic hydroxyl group is alkylated using a Mitsunobu etherification reaction that employs a suitably protected (such as N-Boc) amino alcohol, triphenylphoshine and a dialkyl azodicarboxylate in solvents such as THF or toluene at −15° to 25° C. The Boc protecting group is then removed with a strong acid to provide the appropriate amine salt. The amine is coupled to a benzoic acid derivative under standard amide bond coupling conditions. Hydrogenation of the resulting amide using a palladium catalyst in a solvent such as EtOAc or methanol effects deprotection of the Cbz and benzyl ester groups. Macrolactamization of the resulting amino acid is effected by the addition of a coupling agent, such as the BOP reagent, in a dilute solution of a solvent such as dichloromethane containing a tertiary amine base. The resulting macrolactam ester is reduced with a hydride reducing reagents such as LiBH₄ in THF to give the desired primary alcohols. These alcohols may be oxidized with an oxidizing reagent such as

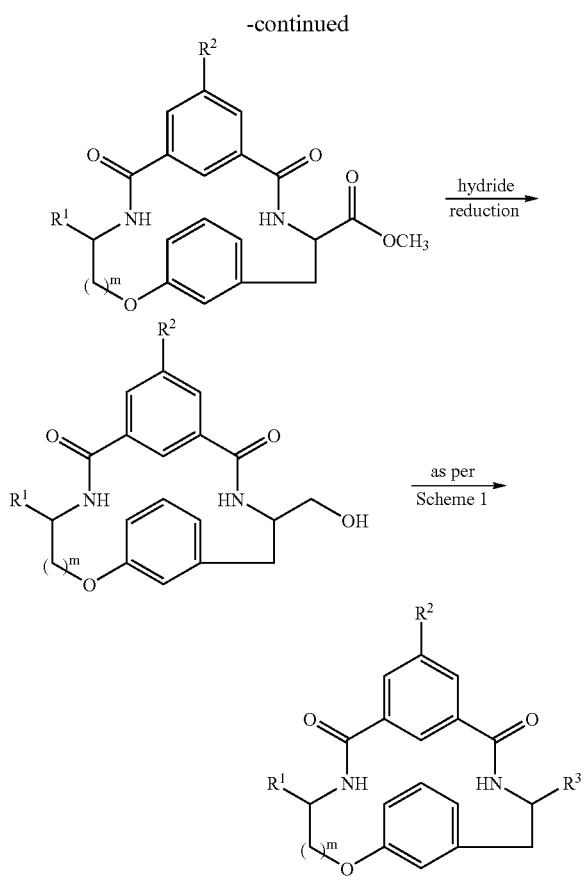

Referring to Scheme 2, m-tyrosine is alternatively converted as described to provide the desired final products. Meta-tyrosine ester is coupled to a benzoic acid derivative under standard amide bond coupling conditions to provide the desired amide ester. The phenolic hydroxyl group is alkylated with an alkylating agent (such as N-Boc-2-bromoethyl amine) and a base (such as potassium carbonate) in a non-reactive solvent such as acetonitrile or DMF. The Boc protecting group is then removed with a strong acid to provide the appropriate amine salt. The aromatic benzyl ester is converted to the corresponding carboxylic acid by a standard hydrogenolysis reaction. Macrolactamization of the resulting amino acid is effected by the addition of a coupling agent, such as the BOP reagent, in a dilute solution of a solvent such as dichloromethane containing a tertiary amine base. The resulting macrolactam ester is reduced with a hydride reducing reagents such as $LiBH_4$ in THF to give the desired primary alcohols. These alcohols may be oxidized with an oxidizing reagent such as $SO_3$ pyridine in DMSO. The macrocyclic aldehyde can be reductively aminated with an amine and a reducing agent such as $NaBH_3CN$ in a methanolic solvent. The aldehyde may also be reacted with an organometallic agent such as an alkyllithium or Grignard reagent to give the corresponding secondary alcohol.

The term "substantially pure" means that the isolated material is at least 90% pure, and preferably 95% pure, and even more preferably 99% pure as assayed by analytical techniques known in the art. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangably in this specification. In addition to humans, a variety of other mammals can be treated according to the method of the present invention.

The present invention is further directed to a method for the manufacture of a medicament or a composition for inhibiting β-secretase enzyme activity in humans and animals comprising combining a compound of the present invention with a pharmaceutical carrier or diluent.

The compounds of the present invention have utility in treating, preventing, ameliorating, controlling or reducing the risk of Alzheimer's disease, other diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment, prevention, control, amelioration, or reduction of risk of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, other beta-secretase inhibitors, gamma-secretase inhibitors, HMG-CoA reductase inhibitors, NSAID's including ibuprofen, N-methyl-D-aspartate (NMDA) receptor antagonists, such as memantine, cholinesterase inhibitors such as galantamine, rivastigmine, donepezil, and tacrine, CB-1 receptor antagonists or CB-1 receptor inverse agonists, antibiotics such as doxycycline and rifampin, vitamin E, anti-amyloid antibodies, or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, or as soft gelatin capsules wherein the active ingredient is mixed with water or an oil medium. Aqueous suspensions contain the active materials in admixture with excipients suitable for the manufacture of aqueous suspensions. Such excipients may be suspending agents, dispersing or wetting agents, or the like. The aqueous suspensions may also contain one or more preservatives, coloring agents, flavoring agents, or sweetening agents.

The compositions for oral use may also be prepared as oily suspensions, or in the form of oil-in-water emulsions, or as syrups or elixirs.

The pharmaceutical compositions may be in the form of a sterile injectable aqueous or oleagenous suspension, or may be prepared in the form of a suppository for rectal administration, a topical formulation, and inhalant or as a transdermal patch, according to the knowledge of those skilled in the art of pharmaceutical formulations.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits maybe provided with all necessary materials and ingredients contained therein, or they may contain instructions for using or making materials or components that must be obtained independently by the patient or person administering the drug to the patient.

When treating, preventing, controlling, ameliorating, or reducing the risk of Alzheimer's disease or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. The total daily dosage is from about 1.0 milligrams to about 2000 milligrams, preferably from about 0.1 milligrams to about 20 milligrams per kilogram of body weight. In the case of a 70 kg adult human, the total daily dose will generally be from about 7 milligrams to about 1,400 milligrams. This dosage regimen may be adjusted to provide the optimal therapeutic response. The compounds may be administered on a regimen of 1 to 4 times per day, preferably once or twice per day.

Exemplary unit dosage forms which may be useful for treatment include 10 mg, 25 mg, 50 mg, 75 mg, 100 mg and 150 mg unit dosage forms.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer FRET) assay is employed with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 µM, 10 µM, 1 µM) were included in the reactions mixture (final DMSO concentration is 0.8%). All experiments were conducted at room temperature using the standard reaction conditions described above. To determine the $IC_{50}$ of the compound, competitive equation V0/Vi=1+ [I]/[IC50] were employed to predict the inhibitory potency of the compounds. The errors in reproducing the dissociation constants are typically less than two-fold.

HPLC assay: A homogeneous end point HPLC assay is employed with the substrate (coumarin-CO-REVNFE-VEFR), which is cleaved by BACE 1 to release the N-terminal fragment attached with coumarin. The Km of the substrate is greater than 100 µM and can not be determined due to the limit of solubility of the substrate. A typical reaction contains approximately 2 nM enzyme, 1.0 µM of the substrate, and buffer (50 mM NaOAc, pH 4.5, 0.1 mg/ml BSA, 0.2% CHAPS, 15 mM EDTA and 1 mM deferoxamine) in a total reaction volume of 100 µl. The reaction is proceeded for 30 min and the reaction is stopped by the addition of 25 µl of 1 M Tris-HCl, pH 8.0. The resulting reaction mixture was loaded on the HPLC and the product was separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at room temperature using the standard reaction conditions described above. To determine the $IC_{50}$ of the compound, four parameters equation is employed for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 1 nM to 1 µM. Such a result is indicative of the intrinsic activity of the compounds in use as inhibitors of beta-secretase enzyme activity.

Several methods for preparing the compounds of this invention are illustrated in the following Schemes and Examples. Starting materials are made according to procedures known in the art or as illustrated herein. The following examples are provided so that the invention might be more fully understood. These examples are illustrative only and should not be construed as limiting the invention in any way.

Intermediate 1

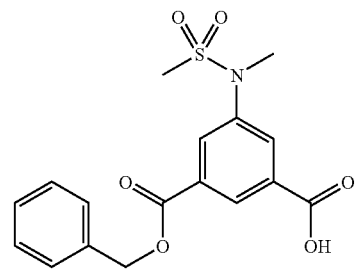

Step A. To a stirred slurry of dibenzyl 5-aminoisophthalate (12.3 g, 34.1 mmol) in 200 mL CH$_2$Cl$_2$/pyridine (3:1) at 0° C. was added methanesulfonyl chloride (2.65 mL, 34.1 mmol). The resulting mixture was stirred for 4 h at room temperature then extracted with 1 N HCl (3×25 mL), water (50 mL), and brine (25 mL). The solution was dried over MgSO$_4$ and evaporated to leave 15.0 g (100%) of the crude sulfonamide as an off-white solid that was used in the next step without further purification.

Step B. To a 0° C. solution containing 15.0 g (34.1 mmol) of sulfonamide intermediate 1-A and 3.1 mL (51.2 mmol) of iodomethane in 100 mL DMF was added sodium hydride (818 mg, 34.1 mmol). After 1 hr the reaction was diluted with 500 mL of ether and quenched with 1N HCl (50 mL). The organic phase was separated and washed with H$_2$O (7×50 mL) then brine. The organic extracts were dried over MgSO$_4$ and evaporated to give 15.1 g (98%) of the N-methylsulfonamide. $^1$H NMR (CDCl$_3$) δ 8.61 (s, 1H), 8.25 (s, 2H), 7.55-7.23 (m, 10H), 5.39 (s, 4H), 3.37 (s, 3H), 2.84 (s, 3H).

Step C. Diester (4.1 g, 9.05 mmol) from step B was dissolved in 90 mL of THF and cooled to 0° C. 0.1 N LiOH (90.5 mL, 9.05 mmol) was added and the reaction was allowed to warm to RT over 16 hours. The solution was acidified with 1N HCl (30 mL) and extracted with EtOAc (3×50 mL). The combined organic extracts were washed with brine and dried over MgSO$_4$, filtered and concentrated in vacuo. Purification on silica gel (95:5:1 DCM/MeOH/HOAc) gave the mono acid 2.69 g (82%) as a white solid. $^1$H NMR (CDCl$_3$ w/5% DMSO $_{d6}$) δ 8.60 (s, 1H), 8.21 (s, 2H), 7.45-7.20 (m, 5H), 5.35 (s, 2H), 3.37 (s, 3H), 2.84 (s, 3H).

EXAMPLE 1 (METHOD A)

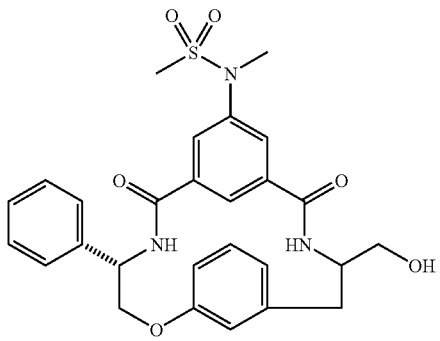

Step A. A 0° C. solution containing 32.0 g (177.0 mmol) of dl-meta tyrosine in 600 mL of MeOH was treated slowly with 12.9 mL (177.0 mmol) of SOCl$_2$. The reaction was then heated to reflux over 16 h, cooled and evaporated to give 35.1 g (86%) of the corresponding methyl ester HCl salt. LCMS (M+1)=196.2.

Step B. To a solution of 7.6 g (33 mmol) of amine 1-A in 200 mL of DCM was added 9.2 mL (66 mmol) of Et$_3$N then 9.4 g (33 mmol) of Cbz anhydride. After stirring for 17 h, the reaction mixture was washed with 1 N HCl (2×50 mL), water (50 mL), and brine (50 mL). The solution was dried, evaporated and chromatographed (7:3 Hexane/EtOAc) to afford 7.27 g (67%) of the title compound as a white solid. $^1$H NMR (CDCl$_3$) δ7.35 (m, 5H), 7.13 (t, J=7.8 Hz, 1 H), 6.71 (dd, J=2.1, 8.0 Hz, 1H), 6.64 (dd, J=2.1, 8.0 Hz, 1H), 6.57 (s, 1H), 5.64 (bs, 1H), Hz, 1H), 5.11 (m, 2H), 4.63 (m, 1H), 3.67 (s, 3H), 3.05 (dq, 2H). LCMS (M-44)=286.2.

Step C. A −15° C. solution containing 5.5 g (16.7 mmol) of phenol 1-B, 4.1 g (17.2 mmol) of N-Boc-L-phenylglycinol and 6.7 g (25.5 mmol) of triphenylphosphine in 50 mL of THF was treated dropwise with 4.76 g (23.6 mmol) of diisopropyl azodicarboxylate. The reaction was stirred to RT over 72 h then concentrated and chromatographed (4:1 Hexanes/EtOAc) to afford 4.49 g (49%) of the desired Mitsunobu product. LCMS [M-Boc]=449.1

Step D: A 0° C. solution containing 4.0 g (7.29 mmol) of the boc protected amine 1-C in 100 mL of EtOAc was subjected to a steady stream of HCl gas for 5 minutes. The reaction was allowed to stir at this temperature for 1 h then concentrated in vacuo. The resulting solid (3.2 g, 99%) was dried under high vacuum for 2 days and used directly in the next step without further purification. $^1$H NMR (DMSO d$_6$)δ 8.64 (bs, 2H), 7.81 (d, J=7.2 Hz, 1H), 7.57 (d, J=6.9 Hz, 1H), 7.51 (m, 2H), 7.36-7.19 (m, 4H), 6.95 (s, 1H), 6.87 (d, J=7.1 Hz, 1 H), 4.94 (q, 7.3 Hz, 2H), 4.78 (bs, 1H), 4.22 (bs, 2H), 3.65 (s, 3H), 3.02 (dd, J=4.7, 13.7 Hz, 1H), 2.83 (t, 1H). LCMS [M+1]=449.1.

Step E: A solution containing 1.36 g (3.03 mmol) of the amine 1-D in 30 mL of CH$_2$Cl$_2$ was treated sequentially with BOP reagent (1.34 g, 3.03 mmol), carboxylic acid intermediate C (1.10 g, 3.03 mmol), and diisopropylethylamine (1.8 mL, 10.6 mmol). The reaction mixture was stirred at ambient temperature for 1 h then washed sequentially with 1 N HCl (2×10 mL), saturated NaHCO$_3$ (2×10 mL), and brine (10 mL). Evaporation of the solvent and silica gel chromatography (1:1 Hexanes/EtOAc) provided 2.10 g (87%) of amide I-E. LCMS [M+1]=794.0.

Step F. To a solution of amide 1-E (794 mg, 1.0 mmol) and 350 mg of 10% Pd(C) in 20 mL of EtOAc and 4 mL of MeOH was stirred at room temperature under a balloon of hydrogen gas for 4 h. The mixture was filtered through a pad of Celite with 30 mL of MeOH, and concentrated to afford 541 mg (95%) of the desired amino acid I-F. LCMS [M+1]= 570.0.

Step G. To a dilute solution containing amino acid 1-F (251 mg, 0.44 mmol) in 250 mL of DCM was added DIPEA (0.15 mL, 0.88 mmol) and 194 mg (0.44 mmol) of BOP reagent. The reaction was stirred at RT for 72 h and evaporated to a solid. Column chromatography (7:3 Hexanes/EtOAc) afforded a 2:1 mixture of macrocyclic amide diastereomers I-G (152 mg, 62%) as a white solid. $^1$H NMR (CDCl$_3$)δ 7.92 (s, 0.66 H), 7.89 (s, 0.33 H), 7.85 (s, 1H), 7.61 (s, 1H), 7.51 (m, 7.49 (m, 6H), 7.05 (s, 1H), 7.00-6.76 (m, 3H), 6.61 (d, J=8.9 Hz, 0.66 H), 6.28 (d, J=9.0 Hz, 0.33 H), 4.81(dd, J=2.3, 10.1 Hz, 0.33 H), 4.56 (dd, J=3.9, 10.9 Hz, 0.66 H), 4.35 (t, 1H), 3.93 (s, 3H), 3.27 (s, 3H), 3.22 (m, 2H), 2.81 (s, 3H). LCMS [M+1]=552.1.

Step H. A solution containing 52 mg (0.1 mmol) of ester 1-G in 1.0 mL of THF was treated with 0.2 mL (0.4 mmol) of 2M LiBH$_4$ in THF. The reaction was stirred for 10 minutes and quenched by the addition of 1 mL of MeOH. After effervescence had ceased, the solution was chromatographed by reverse phase chromatography to afford 39 mg (75%) of the desired macrocyclic alcohol as a white solid. $^1$H NMR (CDCl$_3$ w/5% DMSO$_{d6}$) δ 8.20 (d, J=9.5 Hz, 1H), 7.78 (s, 1H), 7.75 (s, 1H), 7.59 (d, J=7.3 Hz, 1H), 7.50 -7.30 (m, 6H), 7.25 (t, 1H), 7.11 (s, 1H), 6.95 (d, J=8.0 Hz, 1H), 6.81 (d, J=8.0 Hz, 1H), 5.56 (bt, 1H), 4.66 (dd, J=4.8, 6.4 Hz, 1H), 4.51 (dd, J=3.3, 11.4 Hz, 1H), 4.25 (m, 1H), 3.84 (m, 1H), 3.75 (m, 1H), 3.31 (s, 3H), 3.07 (m, 1H), 2.90 (m, 1H), 2.86 (s, 3H). LCMS [M+1]=524.0

EXAMPLE 2

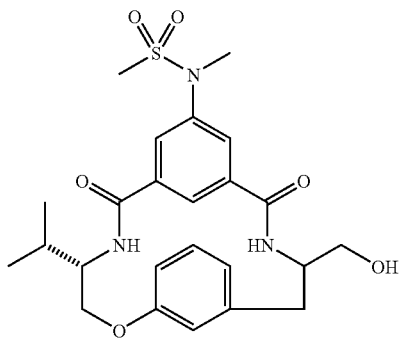

The title compound was prepared by following the procedure outlined for the synthesis of Example 1-H but substituting N-Boc-L valinol as the Mitsunobu reactant in step C.

EXAMPLE 3

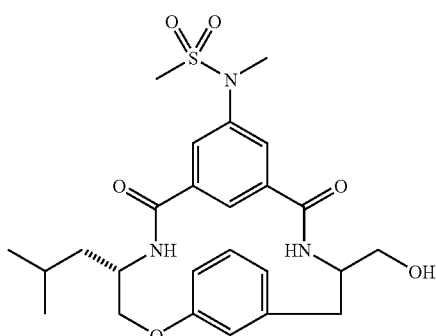

The title compound was prepared by following the procedure outlined for the synthesis of Example 1-H but substituting N-Boc-L-leucinol as the Mitsunobu reactant in step C.

EXAMPLE 4

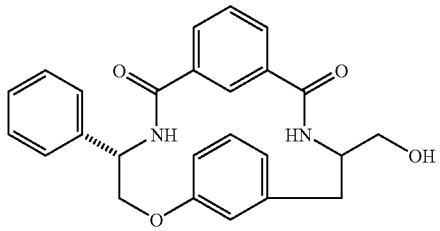

The title compound was prepared by following the procedure outlined for the synthesis of Example 1-H but substituting Isophthalic acid mono benzyl ester as the coupling partner in step E. LCMS [M+1]=417.1.

EXAMPLE 5

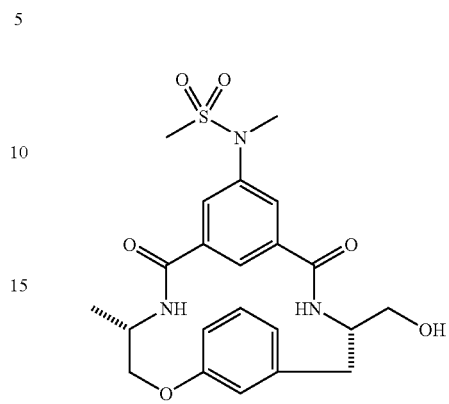

The title compound was prepared by following the procedure outlined for the synthesis of Example 1-H but substituting N-Boc-L-alaninol as the Mitsunobu reactant in step C. LCMS [M+1]=462.2.

EXAMPLE 6

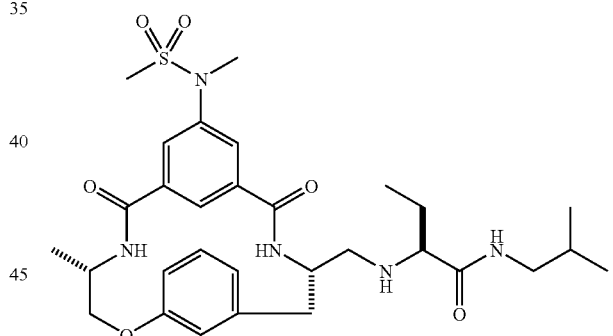

Step A: A solution containing 23 mg (0.05 mmol) of Example 5 in 1 mL of dry DMSO was treated with excess $Et_3N$ and $SO_3$ pyridine reagent. The resulting reaction mixture was stirred at RT for 3 h and diluted with 100 mL of EtOAc. The solution was washed with water (5×5 mL) and brine (5 mL), dried ($MgSO_4$) and concentrated to give the crude aldehyde that was used without further purification. LCMS [M+1]=460.0.

Step B: Crude aldehyde from Example 6-A (4.6 mg, 0.01 mmol) in 2 mL of dry MeOH was treated with 9.7 mg (0.05 mmol) of (S)-isobutyl 2-aminobutyric amide HCl salt then 0.60 mg (0.01 mmol) of $NaBH_3CN$. The reaction mixture was stirred over 17 h at RT and chromatographed without workup on a reverse phase HPLC column to afford 0.71 mg (12%) of the desired compound. LCMS [M+1]=602.1.

EXAMPLE 7 (METHOD B)

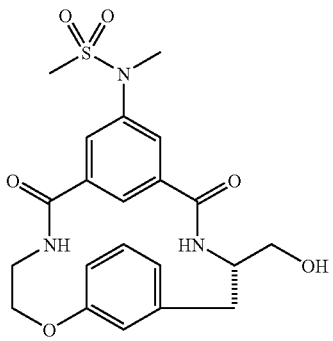

Step A. A solution containing 2.29 g (6.29 mmol) of the carboxylic acid from intermediate 1-C, 1.62 g (6.92 mmol) of (S)-m-tyrosine methyl ester HCl, 2.92 g (6.92 mmol) of benzotriazol-1-yloxytris(dimethylamino)-phosphonium hexafluorophosphate, and 2.44 g (18.87 mmol) of N,N-diisopropylethylamine in 50 mL $CH_2Cl_2$ was stirred at room temperature for 1 h. The solvent was removed in vacuo and the residue was purified by silica gel chromatography (2:3 Hexanes/EtOAc) to provide the desired amide (1.61 g, 47%). LCMS [M+1]=541.1

Step B. A solution containing 1.4 g (2.59 mmol) of the amide from Example 7 Step A, 2-(Boc-amino)ethyl bromide (870 mg, 3.88 mmol), and $Cs_2CO_3$ (1.26 g, 3.88 mmol) in 10 mL DMF was heated to 50° C. for 12 h. The solution was cooled, diluted with $H_2O$ (50 mL), and extracted with ethyl acetate (3×50 mL). The combined organic extracts were rinsed with $H_2O$ (2×50 mL) then brine (50 mL) and dried over $MgSO_4$. Purification by silica gel chromatography (2:3 Hexanes/EtOAc) afforded the phenyl ether (1.05 g, 59%). LCMS [M+1]=584.1.

Step C. A solution containing 1.05 g (1.53 mmol) of the phenyl ether from Example 7 Step B in MeOH (20 mL) was degassed under vacuum. $Pd(OH)_2$ (500 mg) was added and the solution was stirred under a atmosphere of $H_2$ for 1 h. The solution was filtered though celite and concentrated in vacuo to give the carboxylic acid (905 mg, 99%). LCMS [M+1]=594.2.

Step D. The residue from Example 7 Step C was dissolved in $CH_2Cl_2$ (15 mL) and TFA (10 mL) was added. The solution was stirred at RT for 1 h followed by concentration in vacuo to afford the amino acid VII-D. LCMS [M+1]= 494.1.

Step E. The crude residue from Example 7 Step D was subsequently dissolved in $CH_2Cl_2$ (10 mL) and free-based with DIPEA (170 mg, 1.3 mmol). The amino acid solution was then added dropwise to a solution of BOP reagent (427 mg, 1.01 mmol) and DIPEA (170 mg, 1.3 mmol) in $CH_2Cl_2$. The solution was stirred 2 h after the addition was complete. The solvent was then evaporated, the residue was dissolved in ethyl acetate (50 mL) and washed with 1N HCl (2×30 mL), sat. $NaHCO_3$ (1×30 mL), and brine (1×30 mL). The organic layer was dried over $MgSO_4$, filtered and purified by reverse phase HPLC to afford the desired macrolactam (78 mg, 30%). LCMS [M+1]=490.04

Step F. To a solution of the macrolactam ester (67 mg, 0.14 mmol) from Example 7 Step E in THF (5 mL) was added $LiBH_4$ (0.21 mL, 0.42 mmol). The solution was heated to 50° C. for 30 min. The reaction was quenched with MeOH (2 mL) and concentrated in vacuo. Purification by reverse phase HPLC afforded the macrocyclic alcohol (33 mg, 52%). LCMS [M+1]=448.03 $^1$H NMR ($CD_3OD$) δ 7.75 (d, J=12 Hz, 2 H), 7.24 (t, J=8.2 Hz, 1H), 7.16 (s, 1 H), 6.95-6.88 (m, 3H), 4.40 (t, J=8.5 Hz, 1H), 4.31-4.24 (m, 2H), 3.87 (d, J=15.0 Hz, 1H), 3.75-3.31(m, 2H), 3.34 (s, 3H), 3.16 (dd, J=13, 4.5 Hz, 1H) 2.89 (s, 3H), 2.83-2.63 (m, 2H).

EXAMPLE 8

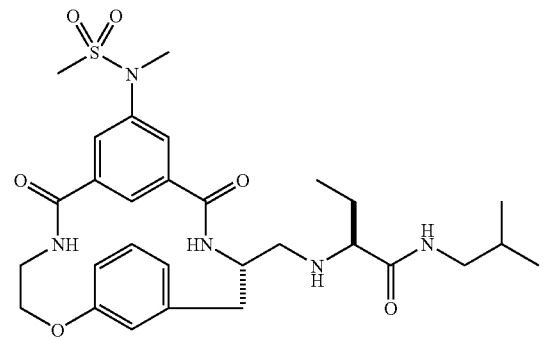

Step A: To 10.0 mg (0.022 mmol) of the macrocyclic alcohol (Example 7 Step F) in DMSO:$CH_2Cl_2$ (3:1, 4 mL) was added triethylamine (22 mg, 0.22 mmol) followed by $SO_3$•pyridine complex. The reaction mixture was stirred at RT for 1 h. The solution was diluted with $H_2O$ (30 mL) and extracted with ethyl acetate (3×30 mL). The combined organic layers were washed sequentially with 1N HCl (20 mL), $H_2O$ (20 mL), and brine (20 ml) then dried over $MgSO_4$, filtered and concentrated in vacuo. The crude material was used without further purification.

Step B: The crude aldehyde prepared above was dissolved in MeOH (3 mL). Isobutyl (S)-2-aminobutyric amide was added followed by $NaCNBH_3$. The reaction was stirred at RT for 12 h. Evaporation of the solvent and purification by reverse phase HPLC afforded the macrocyclic reduced amide (11 mg, 88%). LCMS [M+1]=588.2 $^1$H NMR ($CD_3OD$) δ 8.10 (br, 1H), 7.69 (m ,2H), 7.28 (br, 1H), 7.20 (br, 1H), 6.96-6.84 (m, 2H), 4.40 (m, 2H), 3.91 (br, 1H), 3.55 (br, 1H), 3.40-3.10 (m, 5H), 3.33 (s, 3H), 2.90 (s, 3H), 2.0 (m, 2H), 1.90 (br, 1H), 1.41-0.98 (m, 6H), 0.91 (d, 6H).

EXAMPLE 9

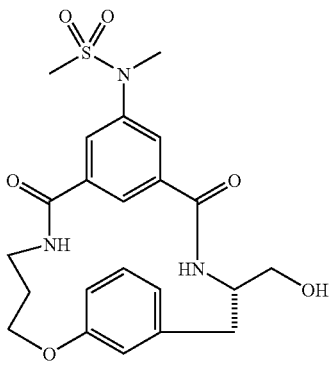

The title compound was prepared in a similar manner to that of Example 7 except 3-(boc-amino)propyl iodide was used as the alkylating agent in step B. LCMS [M+1]=462.07

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of the formula I:

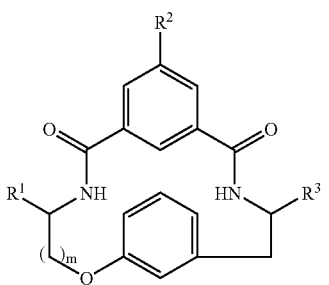

I wherein:
$R^1$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
(a) halo,
(b) hydroxy,
(c) —O—$C_{1-6}$alkyl,
(d) —$C_{3-6}$cycloalkyl,
(e) phenyl or biphenyl, which is unsubstituted or substituted with 1-5 substituents where the substituents are independently selected from:
(i) —$C_{1-6}$alkyl,
(ii) —$C_{3-6}$cycloalkyl,
(iii) —O—$C_{1-6}$alkyl,
(iv) halo,
(v) hydroxy,
(vi) —$CF_3$,
(vii) —$OCF_3$,
(viii) —$NR^9R^{10}$, and
(ix) —CN,
(f) —$CO_2R^9$, wherein $R^9$ is independently selected from:
(i) hydrogen,
(ii) —$C_{1-6}$alkyl, which is unsubstituted or substituted with 1-6 fluoro,
(iii) benzyl, and
(iv) phenyl,
(g) —$NR^9R^{10}$, wherein $R^{10}$ is independently selected from:
(i) hydrogen,
(ii) —$C_{1-6}$alkyl, which is unsubstituted or substituted with 1-6 fluoro,
(iii) benzyl, and
(iv) phenyl,
(h) —$CONR^9R^{10}$,
(3) phenyl which is unsubstituted or substituted with 1-5 substituents where the substituents are independently selected from:
(a) —$C_{1-6}$alkyl,
(b) —$C_{1-6}$alkyl-phenyl,
(c) —$C_{3-6}$cycloalkyl,
(d) —O—$C_{1-6}$alkyl,
(e) halo,
(f) hydroxy,
(g) —$CF_3$,
(h) —$OCF_3$,
(i) —$NR^9R^{10}$, and
(j) —CN;
$R^2$ is selected from the group consisting of:
(1) hydrogen,
(2) $R^4$—$S(O)_p$—,
wherein $R^4$ is independently selected from the group consisting of:
(a) —$C_{1-6}$alkyl, which is unsubstituted or substituted with 1-6 fluoro,
(b) phenyl, and
(c) benzyl,
and wherein p is independently 0, 1, or 2,
(3) $R^4$—$S(O)_pN(R^5)$—,
wherein $R^5$ is independently selected from the group consisting of:
(a) hydrogen,
(b) —$C_{1-6}$alkyl, which is unsubstituted or substituted with 1-6 fluoro,
(c) phenyl, and
(d) benzyl,
(4) —CN,
(5) —$C_{1-6}$alkyl-CN,
(6) halogen, (7)

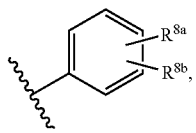

wherein $R^{8a}$ and $R^{8b}$ are independently selected from the group consisting of:
(a) hydrogen,
(b) —CN,
(c) halo,
(d) —$C_{1-6}$alkyl,
(e) —O—$R^5$,
(f) —S—$R^5$,
(g) —$CO_2R^5$, and
(h) tetrazolyl, (8)

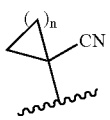

wherein n is 1, 2, 3 or 4;
$R^3$ is selected from the group consisting of:
(1) —CH(OH)—$R^6$,
(2) —C(O)$R^6$,
(3) —CH($R^6$)—$NR^7R^9$, and
(4) —C(O)—$NR^7R^9$;
$R^6$ is independently selected from the group consisting of:
(1) hydrogen
(2) $C_{1-6}$ alkyl, (3)

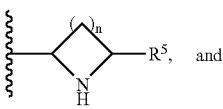

(4)

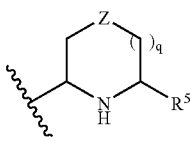

wherein Z is selected from the group consisting of
—C(O)—, —CH(OH)—, and

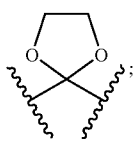

and wherein q is 1 or 2;
$R^7$ is selected from the group consisting of:
(1) hydrogen,
(2) —$C_{1-6}$alkyl, —$C_{2-6}$alkenyl, —$C_{2-6}$alkynyl, or —$C_{3-8}$cycloalkyl which is unsubstituted or substituted with 1-7 substituents where the substituents are independently selected from:
(a) halo,
(b) hydroxy,
(c) —O—$C_{1-6}$alkyl,
(d) —$C_{3-6}$cycloalkyl, (e) phenyl or biphenyl, which is unsubstituted or substituted with 1-5 substituents where the substituents are independently selected from:
(i) —$C_{1-6}$alkyl,
(ii) —$C_{3-6}$cycloalkyl,
(iii) —O—$C_{1-6}$alkyl,
(iv) halo,
(v) hydroxy,
(vi) —$CF_3$,
(vii) —$OCF_3$,
(viii) —$NR^9R^{10}$, and
(ix) —CN,
(f) —$CO_2R^9$,
(g) —$NR^9R^{10}$,
(h) —$CONR^9R^{10}$,
(3) —$CHR^5$—$CONR^9R^{10}$,
(4) phenyl which is unsubstituted or substituted with 1-5 substituents where the substituents are independently selected from:
(a) —$C_{1-6}$alkyl,
(b) —$C_{1-6}$alkyl-phenyl,
(c) —$C_{3-6}$cycloalkyl,
(d) —O—$C_{1-6}$alkyl,
(e) halo,
(f) hydroxy,
(g) —$CF_3$,
(h) —$OCF_3$,
(i) —$NR^9R^{10}$, and
(j) —CN;
m is independently 1, 2, 3 or 4;
and pharmaceutically acceptable salts thereof.

2. The compound of claim 1 wherein $R^1$ is selected from the group consisting of:
(1) hydrogen,
(2) —$C_{1-6}$alkyl, which is unsubstituted or substituted with 1-7 substituents where the substituents are independently selected from:
(a) halo,
(b) hydroxy,
(c) —O—$C_{1-6}$alkyl,
(d) —$C_{3-6}$cycloalkyl,
(e) phenyl or biphenyl, which is unsubstituted or substituted with 1-5 substituents where the substituents are independently selected from:
(i) —$C_{1-6}$alkyl,
(ii) —$C_{3-6}$cycloalkyl,
(iii) —O—$C_{1-6}$alkyl,
(iv) halo,
(v) hydroxy,
(vi) —$CF_3$,
(vii) —$OCF_3$,
(viii) —$NR^9R^{10}$, and
(ix) —CN,
(f) —$CO_2R^9$, wherein $R^9$ is independently selected from:
(i) hydrogen,
(ii) —$C_{1-6}$alkyl, which is unsubstituted or substituted with 1-6 fluoro,
(iii) benzyl, and
(iv) phenyl,
(g) —$NR^9R^{10}$, wherein $R^{10}$ is independently selected from:
(i) hydrogen,
(ii) —$C_{1-6}$alkyl, which is unsubstituted or substituted with 1-6 fluoro, (iii) benzyl, and
(iv) phenyl,
(h) —CONR$^9$R$^{10}$,
(3) phenyl which is unsubstituted or substituted with 1-5 substituents where the substituents are independently selected from:
(a) —C$_{1-6}$alkyl,
(b) —C$_{1-6}$alkyl-phenyl,
(c) —C$_{3-6}$cycloalkyl,
(d) —O—C$_{1-6}$alkyl,
(e) halo,
(f) hydroxy,
(g) —CF$_3$,
(h) —OCF$_3$,
(i) —NR$^9$R$^{10}$, and
(j) —CN.

3. The compound of claim 1 wherein R$^1$ is selected from the group consisting of:
(1) hydrogen,
(2) methyl,
(3) isopropyl,
(4) isobutyl, and
(5) phenyl.

4. The compound of claim 1 wherein R$^2$ is:
R$^4$—S(O)$_2$N(R$^5$)—,
wherein R$^4$ is independently selected from the group consisting of:
(a) —C$_{1-6}$alkyl, which is unsubstituted or substituted with 1-6 fluoro,
(b) phenyl, and
(c) benzyl,
and wherein R$^5$ is independently selected from the group consisting of:
(a) hydrogen,
(b) —C$_{1-6}$alkyl, which is unsubstituted or substituted with 1-6 fluoro,
(c) phenyl, and
(d) benzyl.

5. The compound of claim 1 wherein R$^2$ is CH$_3$—S(O)$_2$N(CH$_3$)—.

6. The compound of claim 1 wherein R$^3$ is selected from the group consisting of:
(1) —CH(OH)—R$^6$,
(2) —C(O)R$^6$, and
(3) —CH(R$^6$)—NR$^7$R$^9$.

7. The compound of claim 1 wherein R$^6$ is:

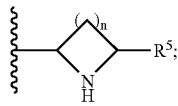

and wherein n is 2 or 3, and R$^5$ is hydrogen or methyl.

8. The compound of claim 1 wherein R$^6$ is:

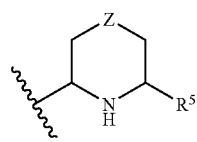

wherein R$^5$ is hydrogen or methyl, and Z is selected from the group consisting of
—C(O)—, —CH(OH)—, and

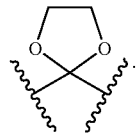

9. The compound of claim 1 wherein R$^3$ is selected from the group consisting of:
(1) —CH$_2$—OH, and
(2) —CH$_2$—NH—CH(CH$_2$CH$_3$)—CO—NH—CH$_2$CH(CH$_3$)$_2$.

10. The compound of claim 1 wherein m is 1.

11. The compound of claim 1 wherein m is 2.

12. A compound which is selected from the group consisting of:

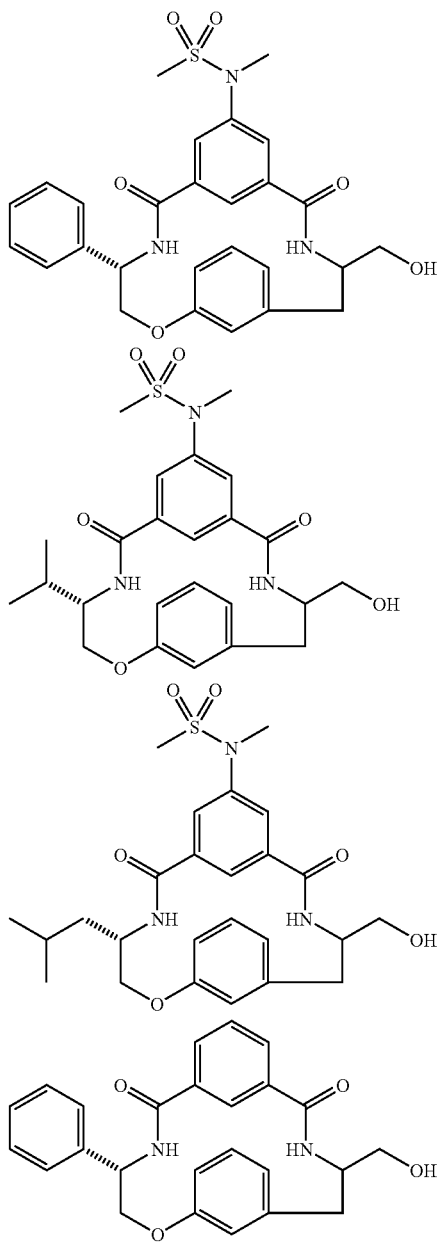

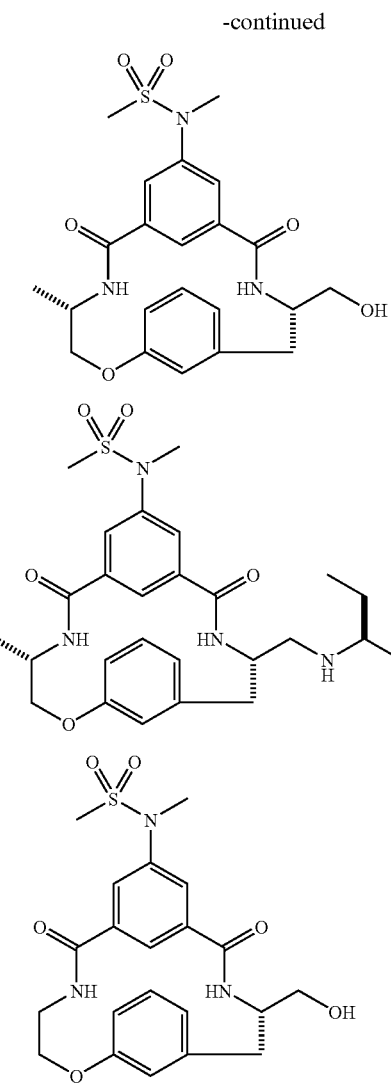
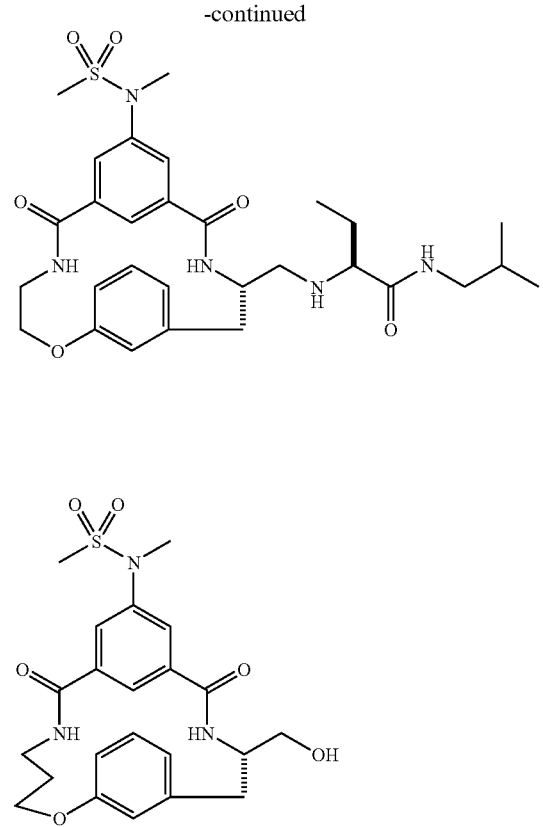
and pharmaceutically acceptable salts thereof.
13. A pharmaceutical composition comprising an effective amount of a compound of claim 1 and a pharmaceutically acceptable carrier.
* * * * *